United States Patent [19]

Esanu

[11] Patent Number: 4,585,776

[45] Date of Patent: Apr. 29, 1986

[54] 4-CHLORO-FURO-(3,4-C)-PYRIDINE DERIVATIVES PROCESS FOR THEIR PREPARATION AND THERAPEUTICAL COMPOSITIONS CONTAINING THEM

[75] Inventor: André Esanu, Paris, France

[73] Assignee: Societe de Conseils de Recherches et d'Applications Scientifiques (S.C.R.A.S.), Paris, France

[21] Appl. No.: 661,376

[22] Filed: Oct. 16, 1984

[30] Foreign Application Priority Data

Oct. 18, 1983 [GB] United Kingdom ............... 8327817

[51] Int. Cl.$^4$ ................... A61K 31/44; C07D 491/048
[52] U.S. Cl. ..................................... 514/302; 546/116
[58] Field of Search ......................... 546/116; 514/302

[56] References Cited

U.S. PATENT DOCUMENTS 4,383,998  5/1983  Esanu .................................. 546/116

Primary Examiner—Henry R. Jiles
Assistant Examiner—Bernard I. Dentz
Attorney, Agent, or Firm—Lucas & Just

[57] ABSTRACT

The invention relates to new 1,3-dihydro-4-chloro-6-methyl-7-hydroxy-furo-(3,4-c)-pyridine derivatives of the formula

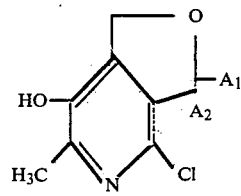

to a preparation process of the same from the corresponding non 4-substituted derivatives and to pharmaceutical compositions useful in selective diuresis and lowering of blood pressure wherein said derivatives are the active ingredients.

4 Claims, No Drawings

4-CHLORO-FURO-(3,4-c)-PYRIDINE DERIVATIVES PROCESS FOR THEIR PREPARATION AND THERAPEUTICAL COMPOSITIONS CONTAINING THEM

The invention relates to new 4-chloro substituted furo-(3,4-c)-pyridine derivatives, to a process for their preparation and to pharmaceutical compositions containing them.

The invention provides 1,3-dihydro-6-methyl-7-hydroxy-furo-(3,4-c)-pyridine derivatives of the general formula I

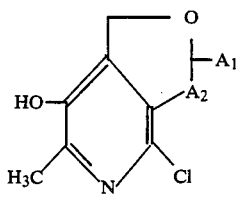

wherein each of $A_1$ and $A_2$ independently represents a hydrogen atom, a straight chain saturated or unsaturated hydrocarbon group having from 1 to 5 carbon atoms, a heterocyclic group having up to 6 ring atoms, a carbomonocyclic group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or an $\alpha$- or $\beta$-alkoxy-N-pyrrolidinyl group in which the alkoxy group has from 1 to 5 carbon atoms.

The compounds according to the invention are of interest for their therapeutical activity, principally in the fields of selective diuresis and lowering of blood pressure. The diuresis induced by these compounds leads to a high elimination rate of $Na^+$ and a low elimination rate of $K^+$.

The invention further provides a process for the preparation of 1,3-dihydro-4-chloro-6-methyl-7-hydroxy-furo-(3,4-c)-pyridine derivatives of the general formula I as above defined, the process comprising treating a compound of the formula II

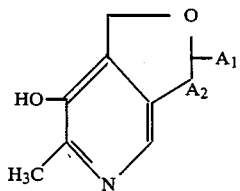

wherein $A_1$ and $A_2$ have the means ascribed to them above, with an excess of N-chlorosuccinimide, to obtain the corresponding 4-chloro-derivative of the general formula I; the reaction is performed between 0° and 15° C. in a non polar solvent such as dichloromethane or tetrahydrofuran.

The invention further provides a pharmaceutical composition comprising a 1,3-dihydro-6-methyl-7-hydroxy-furo-(3,4-c)-pyridine derivative having the general formula I as herein defined in admixture with a pharmaceutically acceptable diluent or carrier.

The starting compounds II may be prepared as described in our U.S. Pat. No. 4 383 998 and U.S. patent application Ser. No. 593700. The invention is illustrated by the following examples.

EXAMPLE 1

1,3-dihydro-3,6-dimethyl-4-chloro-7-hydroxy-furo-(3,4-c)-pyridine

The starting material being the hydrochloride of 1,3-dihydro-3,6-dimethyl-7-hydroxy-furo-(3,4-c)-pyridine, it was first necessary to eliminate the hydrochloric acid before performing the reaction.

Into a two liter reactor fitted with warming, cooling and stirring means, there were poured 22.15 g (0.11 mol) of the starting material and 500 ml of water. After stirring, there was added a sufficient amount of a 10% aqueous solution of sodium bicarbonate to reach pH 7; a white precipitate appeared, and was separated, washed and dried (16.5 g or 0.1 mol).

16.5 g of the base were then treated in a similar reactor with 200 ml of dichloromethane, under stirring, leading to a suspension. This was cooled to 5° C.; there was then slowly added 14.7 g (0.11 mol) of N-chlorosuccinimide and the mixture was stirred for two hours. A white precipitate formed, and was separated, washed, dried and recrystallized from ethanol at 40° C. Yield 16.8 g (84%) of a white crystalline product, elemental analysis of which showed good correspondence with the formula $C_9H_{10}ClNO_2$. Melting point 248° C.

EXAMPLE 2

1,3-dihydro-3-propyl-4-chloro-6-methyl-7-hydroxy-furo-(3,4-c)-pyridine

This compound has been prepared by the method described in Example 1, from 1,3-dihydro-3-propyl-6-methyl-7-hydroxy-furo-(3,4-c)-pyridine. Yield 79% of a product, elemental analysis of which showed good correspondence with the formula $C_{11}H_{14}ClNO_2$. Melting point 242° C.

EXAMPLE 3

1,3-dihydro-3-phenyl-4-chloro-6-methyl-7-hydroxy-furo-(3,4-c)-pyridine

This compound has been prepared by the method described in Example 1 from 1,3-dihydro-3-phenyl-6-methyl-7-hydroxy-furo-(3,4-c)-pyridine. Yield 69% of a crystalline product, elemental analysis of which showed good correspondence with the formula $C_{14}H_{12}ClNO_2$. Melting point 230° C.

EXAMPLE 4

1,3-dihydro-3-p.chlorophenyl-4-chloro-6-methyl-7-hydroxy-furo-(3,4-c)-pyridine

This compound has been prepared by the method described in Example 1, from 1,3-dihydro-3-p.chlorophenyl-6-methyl-7-hydroxy-furo-(3,4-c)-pyridine. Yield 76% of a crystalline product, elemental analysis of which showed good correspondence with the formula $C_{14}H_{11}Cl_2NO_2$. Melting point 218° C.

EXAMPLE 5

1,3-dihydro-3-p.methoxyphenyl-4-chloro-6-methyl-7-hydroxy-furo-(3,4-c)-pyridine This compound has been prepared by the method described in Example 1, from 1,3-dihydro-3-p.methoxyphenyl-6-methyl-7-hydroxy-furo-(3,4-c)-pyridine. Yield 73% of a crystalline product, elemental analysis of which showed good correspondence with the formula $C_{15}H_{14}ClNO_3$. Melting point 204° C.

EXAMPLE 6

1,3-dihydro-3-p.methylthiophenyl-4-chloro-6-methyl-7-hydroxy-furo-(3,4-c)-pyridine This compound has been prepared by the method described in Example 1, from 1,3-dihydro-3-p.thiomethylphenyl-6-methyl-7-hydroxy-furo-(3,4-c)-pyridine. Yield 72% of a crystalline product, elemental analysis of which showed good correspondence with the formula $C_{15}H_{14}ClNO_2S$. Melting point 193° C.

EXAMPLE 7

1,3-dihydro-3-p.trifluoromethylphenyl-4-chloro-6-methyl-7-hydroxy-furo-(3,4-c)-pyridine This compound has been prepared by the method described in Example 1, from 1,3-dihydro-3-p.trifluoromethylphenyl-6-methyl-7-hydroxy-furo-(3,4-c)-pyridine. Yield 81% of a crystalline product, elemental analysis of which showed good correspondence with the formula $C_{15}H_{11}ClF_3NO_2$. Melting point 221° C.

EXAMPLE 8

1,3-dihydro-3-α-furyl-4-chloro-6-methyl-7-hydroxy-furo-(3,4-c)-pyridine

This compound has been prepared by the method described in Example 1, from 1,3-dihydro-3-α-furyl-6-methyl-7-hydroxy-furo-(3,4-c)-pyridine. Yield 71% of a white crystalline product, elemental analysis of which showed good correspondence with the formula $C_{12}H_{10}ClNO_3$. Melting point 187° C.

EXAMPLE 9

1,3-dihydro-3-α-thienyl-4-chloro-6-methyl-7-hydroxy-furo-(3,4-c)-pyridine

This compound has been prepared by the method described in Example 1, from 1,3-dihydro-3-α-thienyl-6-methyl-7-hydroxy-furo-(3,4-c)-pyridine. Yield 70% of a white crystalline product, elemental analysis of which showed good correspondence with the formula $C_{12}H_{10}ClNO_2S$. Melting point 168° C.

EXAMPLE 10

1,3-dihydro-3-phenylethyl-4-chloro-6-methyl-7-hydroxy-furo-(3,4-c)-pyridine

This compound has been prepared by the method described in Example 1 from 1,3-dihydro-3-phenylethyl-6-methyl-7-hydroxy-furo-(3,4-c)-pyridine. Yield 79% of a yellowish crystalline product, elemental analysis of which showed good correspondence with the formula $C_{16}H_{16}ClNO_2$. Melting point 193° C.

EXAMPLE 11

1,3-dihydro-3,3,6-trimethyl-4-chloro-7-hydroxy-furo-(3,4-c)-pyridine

This compound has been prepared by the method described in Example 1, from 1,3-dihydro-3,3,6-trimethyl-7-hydroxy-furo-(3,4-c)-pyridine. Yield 89% of a white crystalline product, elemental analysis of which showed good correspondence with the formula $C_{10}H_{12}ClNO_2$. Melting point 251° C.

EXAMPLE 12

1,3-dihydro-3-phenyl-3,6-dimethyl-4-chloro-7-hydroxy-furo-(3,4-c)-pyridine

This compound has been prepared by the method described in Example 1, from 1,3-dihydro-3-phenyl-3,6-dimethyl-7-hydroxy-furo-(3,4-c)-pyridine. Yield 84% of a white crystalline product, elemental analysis of which showed good correspondence with the formula $C_{15}H_{14}ClNO_2$. Melting point 246° C.

EXAMPLE 13

1,3-dihydro-3-p.chlorophenyl-3,6-dimethyl-4-chloro-7-hydroxy-furo-(3,4-c)-pyridine This compound has been prepared by the method described in Example 1, from 1,3-dihydro-3-p.chlorophenyl-3,6-dimethyl-7-hydroxy-furo-(3,4-c)-pyridine. Yield 87% of a white crystalline product, elemental analysis of which showed good correspondence with the formula $C_{15}H_{13}Cl_2NO_2$. Melting point 233° C.

EXAMPLE 14

1,3-dihydro-3-α-thienyl-3,6-dimethyl-4-chloro-7-hydroxy-furo-(3,4-c)-pyridine This compound has been prepared by the method described in Example 1, from 1,3-dihydro-3-α-thienyl-3,6-dimethyl-7-hydroxy-furo-(3,4-c)-pyridine. Yield 68% of a white crystalline product, elemental analysis of which showed good correspondence with the formula $C_{13}H_{12}ClNO_2S$. Melting point 209° C.

EXAMPLE 15

1,3-dihydro-3-n-pentyl-3-p-toluyl-4-chloro-6-methyl-7-hydroxy-furo-(3,4-c)-pyridine This compound has been prepared by the method described in Example 1, from 1,3-dihydro-3-n-pentyl-3-p-toluyl-6-methyl-7-hydroxy-furo-(3,4-c)-pyridine. Yield 66% of a product, elemental analysis of which showed good correspondence with the formula $C_{20}H_{24}ClNO_2$. Melting point 180° C.

EXAMPLE 16

1,3-dihydro-3,3-diphenyl-4-chloro-6-methyl-7-hydroxy-furo-(3,4-c)-pyridine

This compound has been prepared by the method described in Example 1, from 1,3-dihydro-3,3-diphenyl-6-methyl-7-hydroxy-furo-(3,4-c)-pyridine. Yield 88% of a white crystalline product, elemental analysis of which showed good correspondence with the formula $C_{20}H_{16}ClNO_2$. Melting point 240° C.

EXAMPLE 17

1,3-dihydro-3-(2,3-dichlorophenyl)-3-phenyl-4-chloro-6-methyl-7-hydroxy-furo-(3,4-c)pyridine This compound has been prepared by the method described in Example 1, from 1,3-dihydro-3-(2,3-dichlorophenyl)-3-phenyl-6-methyl-7-hydroxy-furo-(3,4-c)-pyridine. Yield 81% of a white crystalline product, elemental analysis of which showed good correspondence with the formula $C_{20}H_{14}Cl_3NO_2$. Melting point 221° C.

EXAMPLE 18

1,3-dihydro-3-p.trifluoromethylphenyl-3-phenyl-4-chloro-6-methyl-7-hydroxy-furo-(3,4-c)-pyridine This compound has been prepared by the method described in Example 1, from 1,3-dihydro-3-p.trifluoromethylphenyl-3-phenyl-6-methyl-7-hydroxy-furo-(3,4-c)-pyridine. Yield 84% of a white crystalline product, elemental analysis of which showed good correspondence with the formula $C_{21}H_{15}ClF_3NO_2$. Melting point 259° C.

EXAMPLE 19

1,3-dihydro-3-p-pyrrolidinylethoxyphenyl-3-p-chlorophenyl-4-chloro-6-methyl-7-hydroxy-furo-(3,4-c)-pyridine This compound has been prepared by the method described in Example 1, from 1,3-dihydro-3-pyrrolidinylethoxyphenyl-3-p-chlorophenyl-6-methyl-7-hydroxy-furo-(3,4-c)-pyridine. Yield 78% of a white crystalline product, elemental analysis of which showed good correspondence with the formula $C_{26}H_{26}Cl_2NO_3$. Melting point 200° C.

EXAMPLE 20

1,3-dihydro-3-(3,4,5-trimethoxyphenyl-ethyl)-3-α-furyl-4-chloro-6-methyl-7-hydroxy-furo-(3,4-c)-pyridine This compound has been prepared by the method described in Example 1 from 1,3-dihydro-3-(3,4,5-trimethoxyphenyl-ethyl)-3-α-furyl-6-methyl-7-hydroxy-furo-(3,4-c)-pyridine. Yield 58% of a yellowish crystalline product, elemental analysis of which showed good correspondence with the formula $C_{23}H_{25}ClNO_6$. Melting point 197° C.

TOXICITY

Toxicity has been researched on rats and mice, per oral route; no LD 50 could be determined on rats, whereas for mice it was not lower than 4 g/kg.

PHARMACOLOGY

The interest of the compounds of the invention has been evidenced by various pharmacologic tests.

(1°) Study of the urinary elimination in the rat.

This study has been conducted on Wistar male rats weighing 270-280 g.

Ten batches of each twelve animals were used; eight batches by the compounds according to the invention, one batch by tienilic acid as reference compound, all animals of these seven batches at the same dose of 10 mg/kg/day; the tenth batch is for control.

The animals were treated for three days and placed in a metabolic cage fitted for the collection of urines; neither food nor drink was given during the treatment in order to avoid any contamination. The collected volumes of urine are measured after six hours and twenty four hours. After six hours, each animal receives 25 ml/kg of physiologic serum. On the fourth day, the animal receives the last treatment. For all batches Na+ and K+ were measured and the ratio Na+/K+ calculated. The results are reported in the following table.

TABLE

| ADMINISTRATION PER OS OF | VOLUMES (ml) | | | Na/K |
|---|---|---|---|---|
| 10 mg/kg/day | 0-6 h | 6-24 h | 0-24 h | RATIO |
| Control | 6.6 | 11.3 | 17.9 | 1.24 |
| Tienilic acid | 8.4 | 10.8 | 19.2 | 1.51 |
| EX. 2 | 9.0 | 11.3 | 20.3 | 2.24 |
| EX. 3 | 9.9 | 10.8 | 20.7 | 2.53 |
| EX. 4 | 10.8 | 10.8 | 21.6 | 2.80 |
| EX. 7 | 10.1 | 11.6 | 21.7 | 2.37 |
| EX. 12 | 9.9 | 11.4 | 21.3 | 2.87 |
| EX. 15 | 10.9 | 11.8 | 22.7 | 2.46 |
| EX. 17 | 9.6 | 12.0 | 21.6 | 2.55 |
| EX. 18 | 10.0 | 12.4 | 22.4 | 2.39 |

(2°) Action on blood pressure.

This study was conducted on rats suffering from high blood pressure induced by the method of GOLDBLATT in comparison with Indapamine. This method is no longer described, for it is well known and the study shows, at the same therapeutic doses, that the compounds of the invention have, on this test, a similar action on the lowering of blood pressure on the rats.

The major interest of the compounds of the invention rely on the high Na+/K+ ratio which is a very favourable factor. It is well known that a low elimination rate of K+ is benefic to the patient in most cases.

PRESENTATION-POSOLOGY

Although any oral form is suitable, tablets and gelatine capsules containing each 25-100 mg of active ingredient are preferred. Usual posology in human therapy is 50 to 250 mg/day.

I claim:

1. A 1,3-dihydro-6-methyl-7-hydroxy-furo-(3,4-c)-pyridine derivative of the formula wherein each of $A_1$ and $A_2$ independently represents a hydrogen atom, a straight chain saturated hydrocarbon group having from 1 to 5 carbon atoms or a straight chain unsaturated hydrocarbon group having from 2 to 5 carbon atoms, a thienyl group, a furyl group, a phenyl group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or an α- or β-N-pyrrolidinyl-alkoxy group in which the alkoxy group has from 1 to 5 carbon atoms.

2. Preparation process of a 1,3-dihydro-6-methyl-7-hydroxy-furo-(3,4-c)-pyridine derivative of claim 1 comprising treating a compound of the formula:

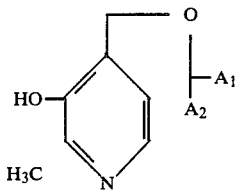

wherein $A_1$ and $A_2$ have the meaning ascribed to them above, with an excess of N-chlorosuccinimide, the reaction being performed between 0° and 15° C. in a non polar solvent.

3. A pharmaceutical composition comprising a diuretically or hypotensively effective amount of a 1,3-dihydro-6-methyl-7-hydroxy-furo-(3,4-c)pyridine derivative as defined in claim 1 in admixture with a pharmaceutically acceptable diluent or carrier.

4. The method of claim 2 wherein the non polar solvent is dichloromethane or tetrahydrofuran.

* * * * *

UNITED STATES PATENT AND TRADEMARK OFFICE
CERTIFICATE OF CORRECTION

PATENT NO. : 4,585,776
DATED : April 29, 1986     Page 1 of 2
INVENTOR(S) : Andre Esanu It is certified that error appears in the above-identified patent and that said Letters Patent is hereby corrected as shown below:

In the Abstract on page 1 of the patent, delete the formula shown and substitute the following therefor:

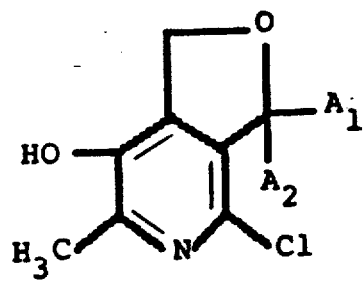

In column 1, delete formula I shown and substitute the following therefor:

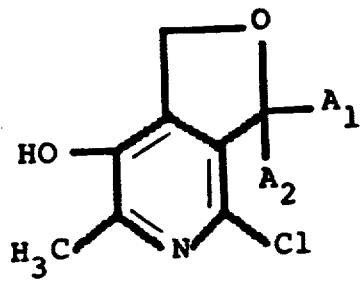

I

UNITED STATES PATENT AND TRADEMARK OFFICE
CERTIFICATE OF CORRECTION

PATENT NO. : 4,585,776
DATED : April 29, 1986
INVENTOR(S) : Andre Esanu

It is certified that error appears in the above-identified patent and that said Letters Patent is hereby corrected as shown below:

In column 1, delete formula II shown and substitute the following therefor:

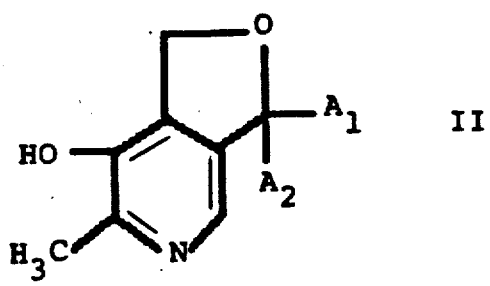   II

Signed and Sealed this

Thirty-first Day of March, 1987

Attest:

DONALD J. QUIGG

*Attesting Officer*   *Commissioner of Patents and Trademarks*